(12) United States Patent
Cervenka et al.

(10) Patent No.: US 8,445,724 B2
(45) Date of Patent: *May 21, 2013

(54) PREPARATION OF IODIXANOL

(75) Inventors: Jan Cervenka, Oslo (NO); Khalid Hussain, Oslo (NO)

(73) Assignee: GE Healthcare AS, Oslo (NO)

( * ) Notice: Subject to any disclaimer, the term of this patent is extended or adjusted under 35 U.S.C. 154(b) by 870 days.

This patent is subject to a terminal disclaimer.

(21) Appl. No.: 11/573,283

(22) PCT Filed: Aug. 8, 2005

(86) PCT No.: PCT/NO2005/000287
§ 371 (c)(1),
(2), (4) Date: Feb. 6, 2007

(87) PCT Pub. No.: WO2006/016815
PCT Pub. Date: Feb. 16, 2006

(65) Prior Publication Data
US 2009/0253935 A1    Oct. 8, 2009

(30) Foreign Application Priority Data
Aug. 9, 2004  (NO) .................................. 20043305

(51) Int. Cl.
*C07C 233/65*     (2006.01)

(52) U.S. Cl.
USPC ........................................ 564/153; 424/9.452

(58) Field of Classification Search
USPC ........................................ 564/153; 424/9.452
See application file for complete search history.

(56) References Cited

U.S. PATENT DOCUMENTS
2008/0214867 A1 *   9/2008   Cervenka et al. ............. 564/153

FOREIGN PATENT DOCUMENTS
WO            99/18054         4/1999
WO            02/083623       10/2002

OTHER PUBLICATIONS

PCT/NO2005/000287 ISR and Written Opinion dated Nov. 16, 2005.

* cited by examiner

*Primary Examiner* — Shailendra Kumar

(57) ABSTRACT

A process for the manufacture of iodixanol by performing a purification process of the crude product in a solvent comprising 1-methoxy-2-propanol. The crude product may be obtained in aqueous solution from dimerization of 5-acetamido-N,N'-bis(2,3-dihydroxypropyl)-2,4,6-triiodo-isophthalamide ("Compound A").

17 Claims, No Drawings

PREPARATION OF IODIXANOL

This application is a filing under 35 U.S.C. 371 of international application number PCT/NO2005/000287, filed Aug. 8, 2005, which claims priority to application number 20043305 filed Aug. 9, 2004, in Norway the entire disclosure of which is hereby incorporated by reference.

This invention is concerned with the manufacture of iodixanol (1,3-bis(acetamido)-N,N'-bis[3,5-bis(2,3-dihydroxypropylaminocarbonyl)-2,4,6-triiodophenyl]-2-hydroxypropane).

Iodixanol is the non-proprietory name of the chemical drug substance of a non-ionic X-ray contrast agent marketed under the trade name Visipaque™. Visipaque™ is one of the most used agents in diagnostic X-ray procedures and is manufactured in large quantities.

The manufacture of such non-ionic X-ray contrast agents involves the production of the chemical drug substance (referred to as primary production) followed by formulation into the drug product (referred to as secondary production). Primary production of iodixanol involves a multi step chemical synthesis and a thorough purification process. For a commercial drug product it is important for the primary production to be efficient and economical and to provide a drug substance fulfilling the specifications, e.g. as expressed on the US Pharmacopea.

A number of methods are known for the preparation of iodixanol. These are all multi step chemical synthetic processes and the cost of the final formulated product thus mainly depends on these processes. It is therefore important to optimize the processes both for economic and environmental reasons.

Three main chemical synthetic processes are known for the preparation of iodixanol, all of which start with 5-nitroisophthalic acid. In the first process described in EP patent 108638, which document is hereby incorporated by reference, the final intermediate 5-acetamido-N,N'-bis(2,3-dihydroxypropyl)-2,4,6-triiodo-isophthalamide (hereinafter "Compound A") is reacted with a dimerisation agent such as epichlorohydrin to yield the drug substance, see Scheme I.

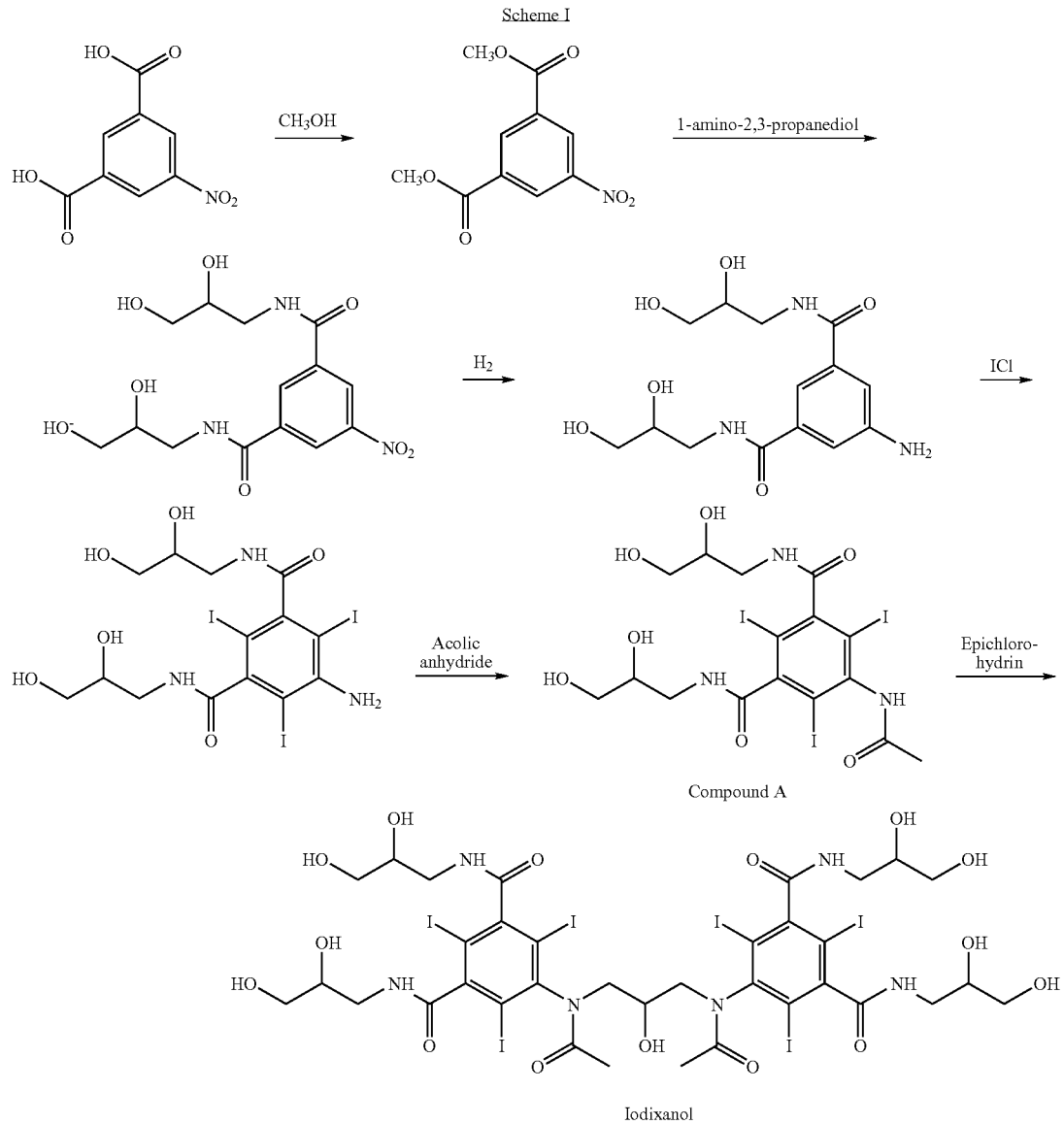

Scheme I

The overall yield in this process is relatively low and the purification of the end product iodixanol is expensive and time consuming. The purification process described in EP patent 108638 involves purification by preparative liquid chromatography. The use of preparative liquid chromatography is a serious disadvantage in industrial processes in particular due to the high costs involved.

Several attempts have been made to find alternative manufacturing processes. Attempts to increase the yield of the chemical synthesis is published by Priebe et. al. (Acta Radiol. 36 (1995), Suppl. 399, 21-31. This publication describes another route which avoids the difficult last step of the process of Scheme I. However, the route involves eight reaction steps from 5-nitroisophthalic acid, which is undesirable, and one of the steps includes chlorination with thionyl chloride, which is extremely corrosive. Also, the introduction of the iodine atoms takes place very early in the sequence, which is disadvantageous as iodine is the most expensive reagent in the process. The yield and final purification method for this route have not been reported.

The third route to iodixanol involves the synthesis of 5-amino-2,4,6-triiodoisophthalic acid (WO 96/37458) and then its dichloride (WO 96/37459), followed by conversion into Compound A (U.S. Pat. No. 5,705,692) and finally dimerisation as in the process of Scheme I. This method thus has the same disadvantages as the first process, and also uses an undesirable acid chlorination step.

Several attempts have been made to find alternative purification procedures avoiding the liquid chromatography method described in European patent 108636.

WO 99/18054 describes a process for the crystallization of i.a. iodixanol where the crystallization is effected with high thermal energy, specifically under elevated pressure and at a temperature above the boiling point of the solution at atmospheric pressure. A number of suitable solvents are listed at page 3 of the document.

WO 00/47549 describes a process for the preparation of iodixanol where unreacted Compound A is precipitated from the reaction mixture and recovered for reuse in a later batch. This increases the overall yield of the process and the removal of most of the unreacted Compound A from the reaction mixture allows the expensive preparative liquid chromatography purification to be replaced by conventional crystallization methods.

When iodixanol is crystallized from a mixture of methanol and 2-propanol (WO 99/18054) with a small amount of residual water under reflux, the crystallization is slow and the purification effect is limited. To achieve the desired purity, the crude iodixanol produced by the synthetic chemical process is crystallized twice. The process is time consuming and takes about 3 days for the first crystallization and about 2 days for the second one.

Methods for the purification of iohexol, the drug substance of another non-ionic X-ray contrast media Omnipaque™, are also described is various publications. Iohexol (5-[N-(2,3-dihydroxypropyl)-acetamido]-N,N'-bis(2,3-dihydroxypropyl)-2,4,6-triiodoisophtalamide) is synthesized from Compound A by N-alkylation of the carboxamide group in good yields. Iohexol is purified by one or more crystallizations. A process for the purification of iohexol by crystallization from the 1-metoxy-2-propanol or mixtures of 1-metoxy-2-propanol with water and/or isopropanol is known from WO02/083623.

It is hence a desire to reach to a purification process where crude iodixanol as obtained by N-alkylation of Compound A as illustrated in Scheme I and hereinafter denoted "dimerisation", can be obtained in a sufficient pure form by a maximum of two crystallization steps and preferable by one single crystallization step. The total crystallization time should be shortened and should not exceed 4 days. It is further desired to achieve improvements of the economy of the purification process by reducing the energy input and the amounts of solvents needed in the process and to achieve a higher output of product per unit reactor volume.

It has now surprisingly been found that using a solvent comprising 1-metoxy-2-propanol in the purification step of crude iodixanol will fulfill one or more of the desired improvements listed above.

In one embodiment the present invention provides a process for the manufacture of iodixanol by performing a purification process of a crude product containing iodixanol in a solvent comprising 1-metoxy-2-propanol. The purification process is preferably a crystallization process.

Further embodiments of the invention are specified in the attached claims.

Crude product is obtained from the processes known from the state of art, e.g. from the dimerisation process illustrated in Scheme I above. The dimerisation step itself may be carried out as described in European patent 108638 and WO 98/23296, for example using epichlorohydrin, 1,3-dichloro-2-hydroxypropane or 1,3-dibromo-2-hydroxypropane as the dimerisation agent. The reaction is usually carried out in a non-aqueous solvent such as a $C_{1-6}$-alcohol, preferably 2-methoxyethanol and/or methanol, and generally results in the conversion of 40 to 60% of Compound A to iodixanol. Dimerisation in pure water or mixtures of water and one or more alcohols (e.g. $C_{1-6}$-alkanols) or in a solvent comprising 1-metoxy-2-propanol is also possible.

Prior to the purification step the crude product is preferably desalinated, removing salt formed during the chemical synthesis and preferably also reduction of the amount of residual starting material (Compound A) is performed. Any organic solvent used during the chemical synthesis should also be reduced if necessary to an amount not interfering substantially with the purification process.

The crude product from the dimerisation and following work-up steps is in aqueous solution with small traces of organic solvent. The crude product contains about 75-90 weight % iodixanol, 3-10 weight % iohexol, 3-7 weight % Compound A and also minor amounts of other impurities. This crude product is the starting material for the further purification, preferably by crystallization, from a solvent comprising 1-metoxy-2-propanol. The work-up procedures are those conventionally used and known from the state of art.

In the purification process, the crude product comprising iodixanol in aqueous solution is adjusted to the desired water content if needed. The water removal may also be performed by distillation or by azeotropic distillation by addition of 1-metoxy-2-propanol. After adjusting the water content to the desired level a calculated amount of 1-metoxy-2-propanol is added and the mixture is preferably seeded with iodixanol crystals. The water content and the amount of 1-metoxy-2-propanol depend on the desired initial supersaturation with respect to iodixanol. The range of 1-metoxy-2-propanol/water should be approximately 1 to 20 g of 1-metoxy-2-propanol per g of water, preferably 1 to 10 g of 1-metoxy-2-propanol per g of water, more preferred 1 to 5 g of 1-metoxy-2-propanol per g of water and even more preferred 1.5 to 3 g of 1-metoxy-2-propanol per g of water. Further, the range of 1-metoxy-2-propanol/crude product should be approximately 0.2 to 4 g of 1-metoxy-2-propanol per g of the crude product and preferably 0.3 to 2 g of 1-metoxy-2-propanol per g of the crude product.

After an initial crystallization period, preferably 0-20 hours and more preferred from 0-12 hours, a further amount of 1-metoxy-2-propanol is added step-wise or continuously usually with increasing rate. When the water content is above the desired final level, it is reduced by azeotropic distillation, preferably using a distillation column. The azeotropic distillation is conducted under suitable conditions while iodixanol is precipitating from the mother liquid. The azeotropic distillation is continued until the water content is in the range of 0.25-0.05 g/g, preferably 0.20-0.10 g/g, of crude product. When the desired water content is reached, and the final amount of 1-metoxy-2-propanol has been added, the suspension is stirred for some time, preferably for 2-20 hours and more preferred for 2-10 hours, to complete the crystallization. The total amount of 1-metoxy-2-propanol is about 0.8-4 g of 1-metoxy-2-propanol per g of the crude product, preferably 1.0 to 2 g of 1-metoxy-2-propanol per g of the crude product. The precipitate, preferably in the form of crystalline product, is collected, filtered and washed, preferably with an alkanol such as methanol. A single purification step will normally be sufficient to obtain iodixanol in a purity satisfying the specification. The total purification process will take from 1 to 4 days, preferably 1 to 3 days and usually about 2 days is adequate.

When a solvent comprising 1-metoxy-2-propanol is used in the purification process, particularly the purification by crystallization, a higher water content in the crude product can be allowed under the initiation of the crystallization process than the water content allowable when using solvents known from the state of art, e.g. solvents such as methanol/isopropanol. Iodixanol at high concentrations in water is a highly viscous solution which is difficult to handle. Higher initial water content, which is possible when using solvents comprising 1-methoxy-2-propanol, mainly avoids the problem of the handling of highly viscous solutions and also saves time and reduces energy consumption. Higher initial water content is also feasible because of the possibility of a subsequent removal of water during the crystallization.

The crystallization processes of the state of art as discussed above are run at a temperature of about 70° C. Higher temperatures promote the kinetics of the crystallization process. By using a solvent comprising 1-metoxy-2-propanol in the crystallization process it is possible to work at temperature above 70° C. at ambient pressure. The optimum working temperature depends on the water content of the solution. At the water contents specified above temperatures in the area of from 100 to 110° C. and more specifically from 102 to 105° C. are feasible. A temperature up to 119° C. which is the boiling point for 1-metoxy-2-propanol at ambient pressure is possible. Even higher temperatures may be employed by increasing the pressure. When optimizing the crystallization temperature, one must also take into account that disintegration of iodixanol or its precursors (Compound A) or side products (iohexol) may occur at the higher temperatures.

It has also been realized that by the use of a solvent comprising 1-metoxy-2-propanol the iodixanol crystals may be obtained in higher purity than is expected. As explained above, the purification process is finalized by filtering the precipitated iodixanol, preferably as crystals, from the solvents and finally washing the crystals with an alkanol such as methanol. The efficiency of the step involving the collection, filtration and washing of the iodixanol product is dependent on the size and shape of the crystals. Surprisingly it has been found that the process of the invention gives crystals that are easier and faster to filter and to wash.

The solvent system used in the purification step will comprise water in addition to 1-methoxy-2-propanol. Optionally, further cosolvents may also be used, e.g. $C_1$ to $C_4$ alkanols such as methanol and/or isopropanol.

In a still further embodiment the invention provides iodixanol as obtained by the process of the invention and where iodixanol is of a purity fulfilling the specification of the US Pharmacopea.

The following non-limiting examples illustrate the invention.

% means weight % if not designated otherwise.

EXAMPLE 1

To a solution of 220 g crude product containing 83.5% iodixanol in 130 ml water was added with 660 ml 1-methoxy-2-propanol and brought to reflux at a temperature of 103 to 105° C. The crude product contained 6.4% of Compound A, 7.9% of iohexol and about 2% of other impurities. Iodixanol seeding crystals were added and the solution was kept under reflux for 40 hours. Water was removed by azeotropic distillation using a simple distillation tower. The water was removed in several small portions from the azeotropic distillate during 2 days. Totally 87 g of water was distilled off in 210 ml of the distillate. After 8 hours of final equilibration under reflux the crystals were filtered off, washed with methanol and dried. 156 g dry crystals of 98.6% purity were isolated, representing 71% yield from the crude product and 85% recovery of iodixanol.

EXAMPLE 2

300 g of dry crude product containing 84.5% of iodixanol 5.4% of Compound A, 7.5% of iohexol and about 3% of other impurities was dissolved in 55 g of water and 165 ml 1-methoxy-2-propanol at 100° C. 2.4 g of crystalline iodixanol seeds were added to the clear solution and the mixture was stirred under reflux during the whole crystallization. After 10.5 hours of the initial equilibration, additionally 331 ml of 1-methoxy-2-propanol was continuously added to the crystallizing mixture during 24.5 hours, following a progressive flow gradient where the flow increased towards the end. After additional 5 hours, almost a constant residual concentration was reached in the mother liquor, and the crystallization was finished. The crystals were separated by filtration, washed with methanol and dried. 214 g of iodixanol crystals of 99.0% purity were obtained representing 71% yield from the crude product and 84% recovery of iodixanol.

EXAMPLE 3

108 kg of an aqueous solution containing 43 kg of the crude product was concentrated by evaporation of the solvent. The crude product contained 83.8% iodixanol, 5.5% of Compound A, 8.2% of iohexol and about 3% of other impurities. 1.7 liter 1-methoxy-2-propanol per kg crude product was added to the concentrate. The water content was adjusted to 0.35 liter water per kg crude product. The solution was then brought to reflux, seeded with 350 g of iodixanol crystals and stirred in 18 hours. Additionally 74.5 liters of 1-methoxy-2-propanol was added in 4 portions during 31 hours. The size of portions was increased towards the end. After further stirring at reflux in about 17 hours, the crystals were separated by filtration and washed with methanol. The purity of the product was 98.8%. The calculated yield was 74% of the crude product and 87% recovery of the iodixanol.

EXAMPLE 4

300 g of dry crude product containing 84.5% of iodixanol, 5.4% of Compound A, 7.5% of iohexol and about 3% of other impurities was dissolved in 54 g of water and 100 ml 1-methoxy-2-propanol at 85° C. The solution was then brought to reflux, seeded with 2.4 g of iodixanol crystals and stirred in 8 hours. Additionally 350 ml of 1-methoxy-2-propanol was added in 4 portions during 30 hours. The size of portions was increased towards the end. After further stirring at reflux in about 10 hours, the crystals were separated by filtration, washed. with methanol and dried. 227 g of iodixanol crystals of 98.9% purity were obtained representing 75% yield from the crude product and 88% recovery of the iodixanol.

The invention claimed is:

1. A process for the manufacture of iodixanol by performing a purification process of a crude product containing about 75-90 weight % iodixanol, 3-10 weight % iohexyl, 3-7 weight % Compound A and minor amounts of other impurities in aqueous solution by crystallization from a solvent comprising 1-methoxy-2-propanol.

2. A process as claimed in claim 1 where crystallization process comprises a single crystallization step.

3. A process as claimed in claim 2 where the total crystallization process time is from 1 to 4 days.

4. A process as claimed in claim 1 where the crystallization process is performed at a temperature of above 70° C.

5. A process as claimed in claim 1 where the range of 1-methoxy-2-propanol/water is approximately 1 to 20 grams of 1-methoxy-2-propanol per gram of water.

6. A process as claimed in claim 5 where the range of 1-methoxy-2-propanol/water is approximately 1 to 10 grams of 1-methoxy-2-propanol per gram of water.

7. A process as claimed in claim 5 where the range of 1-methoxy-2-propanol/water is approximately 1 to 5 grams of 1-methoxy-2-propanol per gram of water.

8. A process as claimed in claim 5 where the range of 1-methoxy-2-propanol/water is approximately 1.5 to 3 grams of 1-methoxy-2-propanol per gram of water.

9. A process as claimed in claim 1 where the range of 1-methoxy-2-propanol/crude product is approximately 0.2 to 4 grams of 1-methoxy-2-propanol per gram of the crude product.

10. A process as claimed in claim 9 where the range of 1-methoxy-2-propanol/crude product is approximately 0.3 to 2 grams of 1-methoxy-2-propanol per gram of the crude product.

11. A process as claimed in claim 1 where the solvent comprises 1-methoxy-2-propanol, water and a cosolvent and where the cosolvent comprise $C_1$ to $C_4$ alkanols.

12. A process as claimed in claim 11 where the cosolvents comprise methanol and/or isopropanol.

13. A process as claimed in claim 1 further comprising filtering and washing the precipitated iodixanol with an alkanol.

14. A process as claimed in claim 2 where the total crystallization process time is about 2 days.

15. A process as claimed in claim 1 where the total crystallization process time is performed at a temperature from about 100 to 110° C.

16. A process as claimed in claim 1 where the total crystallization process time is performed at a temperature from about 102 to 105° C.

17. A process as claimed in claim 13 wherein the alkanol is methanol.

* * * * *